United States Patent [19]

Fellner et al.

[11] 4,377,697

[45] Mar. 22, 1983

[54] IMIDAZOLE HYDRAZONE AND HYDRAZINE DERIVATIVES

[75] Inventors: Peter J. Fellner, Marlow; George Ellames, High Wycombe; Christopher D. Floyd, Prestwood; Paul W. Manley, High Wycombe, all of England

[73] Assignee: G. D. Searle & Co., Skokie, Ill.

[21] Appl. No.: 345,174

[22] Filed: Feb. 2, 1982

[51] Int. Cl.³ .................. C07D 409/04; C07D 233/56
[52] U.S. Cl. ..................................... 548/336; 548/346; 424/273 R
[58] Field of Search ............................... 548/336, 346

[56] References Cited

U.S. PATENT DOCUMENTS 3,621,027 11/1971 Schoen et al. ..................... 548/346

*Primary Examiner*—Robert W. Ramsuer
*Attorney, Agent, or Firm*—Albert Tockman; Robert H. Benson

[57] ABSTRACT

Compounds of the general formulae:

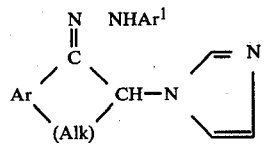

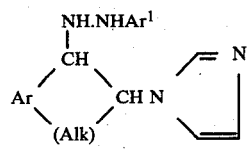

in which Ar and Ar¹ which may be the same or different represent aromatic radicals optionally substituted once or more than by substituents selected from halogen, lower alkyl and lower alkoxy and Alk represents an alkylene group containing from 1 to 4 carbon atoms which alkylene group may be interrupted with a heteroatom; and acid addition salts thereof.

These compounds have anti-anaerobe and also anti-fungal activity and are non-mutagenic.

10 Claims, No Drawings

IMIDAZOLE HYDRAZONE AND HYDRAZINE DERIVATIVES

This invention relates to novel imidazole hydrazone and hydrazine derivatives, to a process for their preparation and to compositions containing them and to their use inter alia in medicine.

It is known that certain compounds such as metronidazole which has the formula:

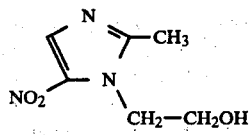

are active against anaerobic bacteria. Published work indicates that the activity is due to the presence of the nitro group. This compound has been reported as being mutagenic and teratogenic.

We have found that certain imidazole hydrazone derivatives of formula I set out below and related hydrazine derivatives of formula II below have anti-anaerobic activity particularly against bacteria which thrive in the absence of air. The activity of these compounds as anti-anaerobes is comparable or superior to metronidazole, whilst they do not appear to be mutagenic. Their superior activity is particularly demonstrated against P.acnes, a bacteria which is associated with acne.

According to the present invention therefore there are provided compounds of the general formulae (I) and (II):

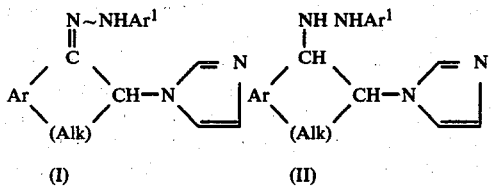

in which Ar and Ar$^1$ represent aromatic radicals which may be substituted one or more times by substituents selected from the following, that is:
halogen,
lower alkyl, and
lower alkoxy;
and Alk represents an alkylene group containing 1–4 carbon atoms which may be interrupted with a heteroatom such as oxygen or sulphur; and acid-addition salts thereof. Suitable salts include hydrochloride, oxalate, sulphate, nitrate, acetate, maleate, citrate and any other pharmaceutically-acceptable salt. It is understood that the term aromatic in relation to the groups Ar and Ar$^1$ includes heteroaromatic.

The wavy-line between the C=N and NHAr$^1$ groups in Formula I indicates the possibility of isomerism. The compounds may be isolated in the form of a mixture of isomers or as the isomers themselves, in particular the E- and Z- isomers and the invention extends to such mixtures and such isomers. In addition compounds of formula II contain two asymmetric centres and it is understood that the invention encompasses the individual isomers and isomer mixtures.

In a preferred class of compounds according to the invention, the group Ar is preferably a phenyl or thienyl group, or alternatively a phenyl or thienyl group substituted by one halogen atom, particularly a chlorine atom.

The group Ar$^1$ is preferably a phenyl group substituted with halogen atoms, in particular chlorine atoms; of such groups 2,4-dichloro, 2,6-dichloro and 2,4,6-trichloro are particularly preferred. Alk is preferably 3–4 carbon atoms. Preferred acid addition salts are the hydrochlorides.

Specific preferred compounds according to the invention are:
(1) 2-Chloro-6-(1H-imidazol-1-yl)-6,7,8,9-tetrahydro-5-benzocycloheptanone, 2,4-dichlorophenylhydrazone;
(2) 6-(1H-Imidazol-1-yl)-6,7,8,9-tetrahydro-5-benzocycloheptanone, 2,4-dichlorophenylhydrazone;
(3) 2-Chloro-6-(1H-imidazol-1-yl)-6,7,8,9-tetrahydro-5-benzocycloheptanone, 2,4,6-trichlorophenylhydrazone;
(4) 6-(1H-Imidazol-1-yl)-7,8,9,10-tetrahydro-5(6H)-benzocyclooctanone, 2,4-dichlorophenylhydrazone;
(5) 7-(1H-Imidazol-1-yl)-4,5,6,7-tetrahydro-8H-cyclohepta[b]-thiophen-8-one, 2,4-dichlorophenylhydrazone;
(6) 6-(1H-Imidazol-1-yl)-7,8,9,10-tetrahydro-5(6H)-benzocyclooctanone, 2,4,6-trichlorophenylhydrazone.

Other specific preferred compounds are those others, the preparation of which is described in the Examples.

As indicated above, the compounds according to the invention have been found to have an action against pathogenic anaerobic bacteria such as Clostridium species, Bacterioides species, and Propionibacterium acnes which is associated with acne. In the case of the two former species this activity is comparable with that of metronidazole whilst against P.acnes their activity is significantly greater than that of metronidazole. The results of in vitro assays for a number of compounds according to the invention are given in Table 1, which follows the Examples.

These tests were conducted by mixing a series of decreasing amounts of the compound under test with a liquid nutrient medium that had been inoculated with one of the test organisms. These preparations were incubated for 24 hours at 37° C. under anaerobic conditions and were then examined for the presence of growth as indicated by the turbidity in the liquid medium. Results were recorded as the lowest concentrations, in mg/l, of test compound that prevented growth of the test organisms (minimal inhibitory concentrations). Each test was run three times and the range of results are indicated.

Additionally the compounds according to the invention have the advantage over metronidazole that they appear to be non-mutagenic in both bacterial Ames tests and mammalian cell transformation assays, (Ames et al., Mutation Res., (1975), 31, 347 and McCann et al., Proc. Nat. Acad. Sci. U.S.A. (1975), 75, 5135) whereas metronidazole is reported to be both mutagneic and teratogenic. This is a very important advantage when one is considering the use of a compound which could be used on a large scale in repetitive therapy.

In addition to the above, the compounds according to the invention have also been found to have an action against non-pathogenic anaerobic bacteria such as Desulfovibrio desulfuricans which is an anaerobe present in oil wells. The use of the compounds of the invention to kill or effectively control such anaerobes is part of the present invention. The results of the in vitro assays for a number of compounds according to the invention against *D. desulfuricans* are given in Table 2 which follows the Examples.

The tests were conducted as described for the pathogenic organisms discussed above.

The compounds according to the invention have also been found to have an action against fungi which is comparable with that of micronazole which has the formula

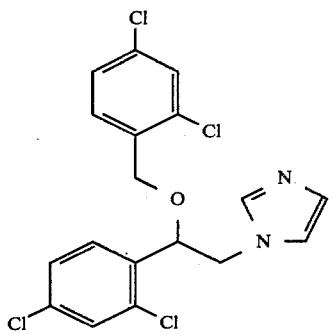

The results of in vitro anti-fungal assay for a number of compounds according to the invention against pathogenic fungi such as those of the Trichophyton species, the Candida species, and *Epidermophyton floccosum* and *Microsporum canis* are tabulated in Table 3 which follows the Examples.

The tests were conducted as described for the anaerobic bacteria with the exception that the organisms were incubated aerobically and kept at 30° C., apart from *C.albicans* which was kept at 37° C. Each test was run in duplicate.

The compounds according to the invention may be prepared by reacting the appropriate ketone of the formula III, (in which Ar, Alk

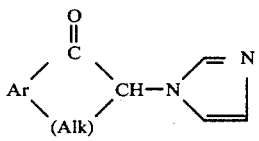

have the above-stated meanings) with the appropriate hydrazine of the formula IV

                                IV (in which $Ar^1$ has the above-stated meaning).

The process is preferably carried out in the presence of a solvent and an acidic catalyst. Either or both of the starting materials may be used in the form of an acid addition salt. The hydrazine may additionally be in the form of a hydrate. The product may be isolated in the form of an acid addition salt or as the free base which may optionally be converted to an acid addition salt.

Preferred temperatures for the reaction are from 20° to 100° C., advantageously from 78° to 80° C. The nature of the solvent is not critical. A preferred solvent is a lower aliphatic alcohol, such as methanol and ethanol. As an acid catalyst, sulphuric or hydrochloric acid may be used.

After reaction, the mixture may be neutralised with alkali, such as sodium bicarbonate and the product recovered by retraction into an organic solvent and isolated by removal of the solvent. Acid addition salts may be made by dissolving the product in a non-aqueous solvent, e.g. diethyl ether, and reacting with a non-aqueous solution of the desired acid.

In the case of the compounds of formula II, these can be prepared from the above described hydrazones by reaction of the hydrazone with reducing agents which reduce the hydrazone linkage. Suitable reducing agents include the organoboranes, for example, the borane.tetrahydrofuran complex ($BH_3.THF$), in a solvent such as tetrahydrofuran at a temperature in the range 0°–50° for 1–3 days. After reaction the solvent may be removed under reduced pressure to leave a residue which is treated with sodium hydrogen carbonate, and the crude product recovered by extraction into an organic solvent and removal of the solvent. The purified product may be isolated following chromatography on silica gel in increasing quantities of chloroform in hexane. Acid addition salts may be made as described for the hydrazone.

The ketones of formula III are known compounds or can be prepared by conventional methods, for example by the method described in P.A.J. Janssen et al., *J. Med.Chem.*, 1969, 12, 781 for 1(4-chlorophenyl)-2-(1H-imidazol-1-yl)ethanone. The hydrazines of formula IV are also known compounds, or can be prepared by conventional methods, i.e. Vogel's Textbook of Practical Organic Chemistry, Longman, London, 1978, p 727.

For administration as a pharmaceutical, one or more compounds according to the present invention are preferably formulated as a composition, that is in association with one or more non-toxic, pharmaceutically acceptable carriers and/or diluents and/or adjuvants. Accordingly, the present invention further provides such a composition and the preparation thereof. Additional medicinal agents may also be present in such compositions if desired. The compositions may be applied topically, orally or by injection.

For topical administration, the composition may be formulated as, for example, a cream, gel or ointment. Such a composition could, for example, be applied topically twice daily for a suitable period, such as two or three weeks. A suitable concentration of active ingredient in the composition could be from 1 to 5% w/w. For vaginal use, the active ingredient may be incorporated in a pessary, or a cream may be used with an applicator, or an impregnated tampon may be utilized.

For oral administration, the pharmaceutical composition may take the form of, for example, a tablet, capsule, suspension or liquid. A typical oral dose may be from 5 to 10 mg/kg body weight once daily, for say, from 2 to 3 weeks.

The active ingredient may also be administered by injection as a composition wherein, for example, saline, dextrose or water for injection may be used as a suitable carrier. An appropriate dose may be from 5 to 10 mg/kg body weight, given once a day for say, from 2 to 3 weeks.

The dose administered and the treatment regimen will be dependent, for example, on the infection, the severity thereof, on the patient being treated and his response to treatment and therefore may be widely varied.

The pharmaceutical compositions may be prepared by techniques well known in the art and described inter alia, in Remington's Pharmaceutical Science, Mach Publishing Co., Easton, Pa. 1965.

The following Examples (in which all temperatures are in degrees Centigrade) illustrate the invention:

EXAMPLE 1

(a)
6-(1H-Imidazol-1-yl)-6,7,8,9-tetrahydro-5-benzocycloheptanone 2,4-dichlorophenylhydrazone 6-(1H-Imidazol-1-yl)-6,7,8,9-tetrahydro-5-benzocycloheptanone (1.46 g) and 2,4-dichlorophenylhydrazine hydrochloride hydrate (1.52 g) were heated together in ethanol (150 ml) under reflux for 7 days at a temperature of 78° C. The solution was evaporated to dryness under reduced pressure and the residue was then treated with saturated aqueous sodium hydrogen carbonate solution and extracted with dichloromethane (3×80 ml). The combined extracts were dried over anhydrous magnesium sulphate and the solvent was evaporated to leave an oil which was chromatographed on silica. Elution with 1% methanol in chloroform gave the hydrazone free base as an oil. A portion of the oil was dissolved in ethyl acetate, the solution warmed to 60° C., and acidified with one equivalent of oxalic acid. On cooling, the solution afforded white platelets of 6-(1H-imidazol-1-yl)6,7,8,9-tetrahydro-5-benzocycloheptanone, 2,4-dichlorophenylhydrazone, hydrogen oxalate, m.p. 185°-187°.

(b)
6-(1H-imidazol-1-yl)-6,7,8,9-tetrahydro-5-benzocycloheptanone, 2,4-dichlorophenylhydrazone, hydrochloride A second portion of the oil obtained in (a) above was dissolved in dichloromethane. The solution was acidified with etheral hydrogen chloride until turbid, and cooled to give, as a white solid, 6-(1H-imidazol-1-yl)-6,7,8,9-tetrahydro-5-benzocycloheptanone, 2,4-dichlorophenylhydrazone, hydrochloride, m.p. 199°-201°.

The following compounds were prepared in an analogous manner.

(c) 2-Chloro-6-(1H-imidazol-1-yl)-6,7,8,9-tetrahydro-5-benzocycloheptanone, 2,4-dichlorophenylhydrazone hydrochloride, m.p. 214°-5°.

(d) 6-(1H-Imidazol-1-yl)-7,8,9,10-tetrahydro-5(6H)-benzocyclooctanone, 2,4-dichlorophenylhydrazone hydrochloride, m.p. 122°-5°.

(e) 3,4-Dihydro-2-(1H-imidazol-1-yl)-1-naphthalenone, 2,4-dichlorophenylhydrazone hydrogen oxalate, m.p. 121°-3°.

(f) 3,4-Dihydro-4-(1H-imidazol-1-yl)-1-benzthiapin-5-(2H-one, 2,4-dichlorophenylhydrazone hydrochloride, m.p. 181°-4°.

(g) 3,4-Dihydro-4-(1H-imidazol-1-yl)-1-benzoxepin-5-(2H)-one, 2,4-dichlorophenylhydrazone hydrochloride, m.p. 180°-2°.

(h) 6-(1H-Imidazol-1-yl)-6,7,8,9-tetrahydro-5-benzocycloheptanone, 2,6-dichlorophenylhydrazone hydrogen oxalate, m.p. 142°-4°.

(i) 3,4-Dihydro-4-(1H-imidazol-1-yl)-1-benzoxepin-5(2H)-one, 2,6-dichlorophenylhydrazone hydrochloride, m.p. 181°-5°.

(j) 7-(1H-Imidazol-1-yl)-4,5,6,7-tetrahydro-8H-cyclohepta[b]-thiophen-8-one, 2,4-dichlorophenylhydrazone hydrogen oxalate, m.p. 104°-6°.

(k) 6-(1H-Imidazol-1-yl)-3-methyl-6,7,8,9-tetrahydro-5-benzocycloheptanone, 2,4-dichlorophenylhydrazone hydrochloride, m.p. 193°-7°.

EXAMPLE 2

(a) 2-(1-Imidazol-1-yl)-1-indanone, 2,4-dichlorophenylhydrazone 2-(1H-Imidazol-1-yl)-1-indanone (6.7 g) and 2,4-dichlorophenylhydrazine hydrochloride (7.0 g) were heated together under reflux in toluene-ethanol (3:1) 250 ml) for 18 hours. The solution was then evaporated to dryness under reduced pressure, treated with sodium hydrogen carbonate solution and extracted with dichloromethane (3×200 ml). The combined extracts were dried over anhydrous magnesium sulphate and the solvents evaporated to leave a gum which was chromatographed on silica. Elution with chloroform gave two solid products which were recrystallised from toluene and indentified as the E- and Z-isomers of 2-(1H-imidazol-1-yl)-1-indanone, 2,4-dichlorophenylhydrazone. One isomer had m.p. 115°-117°, n.m.r. (CDCl$_3$) 2.95 (1H, double doublet, J 7 and 36H$_z$), 3.70 (1H, dd, J 14 and 36H$_z$), 5.55 (1H, dd, J 7 and 14H$_z$) and 6.9-7.8 (11H, multiplet), (Found: C,60.57; H,4.01; N,15.57. C$_{18}$H$_{14}$N$_4$Cl$_2$ requires C,60.52; H,3.95; N,15.68%). The other isomer had m.p. 181°-184°, n.m.r. (CDCl$_3$) 3.17 (1H, dd, J 8 and 33H$_z$), 3.71 (1H, dd, J 15 and 33H$_z$), 5.33 (1H, dd, J 8 and 15H$_z$), 6.7-7.7 (10H, multiplet) and 8.6 (1H,singlet).

The following compound was prepared in an analogous manner from the same ketone and 2,6-dichlorophenylhydrazine:

(b) 2-(1H-Imidazol-1-yl)-1-indanone, 2,6-dichlorophenylhydrazone

One isomer had m.p. 96°-97°, n.m.r. (CDCl$_3$) 2.92 (1H, dd, J 6 and 34H$_z$), 3.71 (1H, dd J 9 and 34H$_z$), 5.55 (1H, dd, J 6 and 9H$_z$), 6.60-7.65 (11H, multiplet), (Found: C,60.67; H,3.99; N,15.54. C$_{18}$H$_{14}$N$_4$Cl$_2$ requires C,60.52; H,3.95; N,15.68%). The other isomer had m.p. 103°-105°, n.m.r. (CDCl$_3$), 2.73 (1H, dd. J 6 and 32H$_z$), 3.17 (1H, dd, J 15 and 32H$_z$), 5.35 (1H, dd, J 6 and 15H$_z$), 7.3-8.1 (11H, multiplet), (Found: C,60.43; H,4.03; N,15.44. C$_{18}$H$_{14}$Cl$_2$ requires C,60.52; H,3.95; N,15.68%).

EXAMPLE 3

(a) 3,4-Dihydro-2-(1H-imidazol-1-yl)-1-naphthalenone, 2,4,6-trichlorophenylhydrazone 3,4-Dihydro-2-(1H-imidazol-1-yl)-1-naphthalenone (1.27 g) and 2,4,6-trichlorophenylhydrazine (1.09 g) in ethanol (150 ml) and a saturated solution of hydrogen chloride in ether (10 ml) were heated together under reflux for 48 hours. The solution was then evaporated to dryness under reduced pressure, treated with sodium hydrogen carbonate solution and extracted with dichloromethane (4×100 ml). The combined extracts were dried over anhydrous magnesium sulphate and the solvent evaporated to leave a gum which was chromatographed on silica. Elution with chloroform gave the hydrazone free base as an oil. The oil was dissolved in ethyl acetate, the solution warmed to 60° and acidified with one equivalent of oxalic acid. On cooling, the solution afforded 3,4-dihydro-2-(1H-imidazol-1-yl)-1-naphthalenone, 2,4,6-trichlorophenylhydrazone, hydrogen oxalate as a white solid, m.p. 173°-175°.

The following compounds were prepared in an analogous manner from the appropriate ketone and the appropriate hydrazine:

(b) 2-Chloro-6-(1H-imidazol-1-yl)-6,7,8,9-tetrahydro-5-benzocycloheptanone, 2,4,6-trichlorophenylhydrazone hydrochloride, m.p. 166°–8°.

(c) 6-(1H-Imidazol-1-yl)-7,8,9,10-tetrahydro-5(6H)-benzocyclooctanone, 2,4,6-trichlorophenylhydrazone hydrochloride, m.p. 178°–182°.

(d) 6-(1H-Imidazol-1-yl)-6,7,8,9-tetrahydro-5-benzocycloheptanone, 2,4,6-trichlorophenylhydrazone hydrogen oxalate, m.p. 87°–91°.

(e) 6,7-Dihydro-5-(1H-imidazol-1-yl)-benzo[b]thiophen-4(5H)-one, 2,4,6-trichlorophenylhydrazone hydrochloride, m.p. 141°–3°.

(f) 2-(1H-Imidazol-1-yl)-1-indanone, 2,4,6-trichlorophenylhydrazone hydrochloride, m.p. 151°–3°.

(g) 3,4-Dihydro-4-(1H-imidazol-1-yl)-1-benzthiapin-5(2H)-one, 2,4,6-trichlorophenylhydrazone hydrochloride, m.p. 94°–6°.

(h) 3-(1H-Imidazol-1-yl)-chroman-4-one, 2,4,6-trichlorophenylhydrazone hydrochloride m.p. 166°–7°.

(i) 3,4-Dihydro-4-(1H-imidazol-1-yl)-1-benzoxepin-5(2H)-one, 2,4,6-trichlorophenylhydrazone hydrochloride, m.p. 198°–200°.

(j) 3,4-Dihydro-4-(1H-imidazol-1-yl)-1-benzoxepin-5(2H)-one, 2,3,4,5,6-pentafluorophenylhydrazone hydrochloride, m.p. 169°–72°.

(k) 6-(1H-Imidazol-1-yl)-6,7,8,9-tetrahydro-5-benzocycloheptanone, 2,3,4,5,6-pentafluorophenylhydrazone hydrochloride, m.p. 124°–6°.

(l) 5-(1H-Imidazol-1-yl)-5,6,7,8-tetrahydro-4H-cyclohepta[b]thiophen-4-one, 2,4,6-trichlorophenylhydrazone hydrogen oxalate, m.p. 113°–6°.

(m) 3,4-Dihydro-2-(1H-imidazol-1-yl)-6-methoxy-1-naphthalenone, 2,4,6-trichlorophenylhydrazone hydrochloride, m.p. 218°–21°.

EXAMPLE 4

N-[2-Chloro-6-(1H-imidazol-1-yl)-6,7,8,9-tetrahydro-5-benzocycloheptyl]-N'-(2,4-dichlorophenyl) hydrazine A solution of borane.tetrahydrofuran complex (BH$_3$.THF) in dry tetrahydrofuran (30 ml, 1M solution) was added dropwise to a solution of 2-chloro-6-(1H-imidazol-1-yl)-6,7,8,9-tetrahydro-5-benzocycloheptanone, 2,4-dichlorophenylhydrazone (4 g) in tetrahydrofuran (250 ml), under an atmosphere of nitrogen, cooled in an ice bath. The reaction mixture was allowed to reach room temperature over two days before treatment with an aqueous solution of sodium hydrogen carbonate and extracted with diethyl ether. The organic phase was dried over anhydrous magnesium sulphate and the solvents evaporated to afford a solid. The solid was dissolved in ethyl acetate, the solution warmed to 60°, and acidified with one equivalent of oxalic acid. On cooling the solution afforded N[2-chloro-6-(1H-imidazol-1-yl)-6,7,8,9-tetrahydro-5-benzocycloheptyl]-N'-(2,4-dichlorophenyl)hydrazine oxalate as a white solid, m.p. 95°–97°.

The following compounds were prepared in an analogous manner:

(b) N-[4-(1H-Imidazol-1-yl)-2,3,4,5-tetrahydro-5-benzoxepinyl]-N'-(2,4-dichlorophenyl)hydrazine dihydrochloride, m.p. 138°–40°.

(c) N-[6-(1H-Imidazol-1-yl)-6,7,8,9-tetrahydro-5-benzocycloheptyl]-N'-(2,6-dichlorophenyl) hydrazine dihydrochloride, m.p. 110°–5°.

The activities of representative compounds according to the invention is given below.

TABLE 1

| | Minimum Inhibitory Concentrations (mg/l) | | |
|---|---|---|---|
| Compound Example No. | Clostridium sporogenes | Bacterioides fragilis | Propionibacterium acnes |
| | (ATCC 19404) | (ATCC 23745) | (ATCC 6919) |
| 1 (b) | 0.5–1.0 | 0.5–1.0 | 2.5 |
| 1 (a) | 0.5–2.5 | 1.0–2.5 | 2.5 |
| 3 (b) | 0.75–1.0 | 0.75–1.0 | 5.0 |
| 1 (d) | 0.5–0.75 | 1.0–2.5 | 0.5–2.5 |
| 1 (j) | 1.0–2.5 | 0.75–1.0 | 5.0 |
| 3 (c) | 0.5–1.0 | 2.5 | 2.5 |
| Metronidazole | 0.5 | 0.5 | >100 |

TABLE 2

| | Minimum Inhibitory Concentrations (mg/l) | | |
|---|---|---|---|
| Compound Example No. | Desulfovibrio desulfuricans | D.desulfuricans | D.desulfuricans |
| | API-CORE | AIP-BREWER | API SW2 |
| 1 (b) | 0.5 | 0.5–0.75 | 0.5–1.0 |
| 1 (a) | 0.5 | 0.5 | 0.5 |
| 3 (b) | 0.75–1.0 | 0.75 | 0.75–2.5 |
| 1 (d) | 0.5–2.5 | 0.5–1.0 | 0.5–0.75 |
| 1 (j) | 0.75–1.0 | 0.5–0.75 | 0.75–1.0 |
| 3 (c) | 0.75–1.0 | 0.5–0.75 | 0.5–0.75 |
| Metronidazole | 0.5 | 0.5 | 0.5 |

TABLE 3

| | Minimum Inhibitory Concentrations (mg/l) | | | | | | | |
|---|---|---|---|---|---|---|---|---|
| Compound Example No. | Trichophyton mentagrophytes | Trichophyton rubrum | Epidermophyton floccosom | Microsporum canis | Candida albicans A | C.albicans B | C.albicans GB | C.albicans 3153 |
| 3 (b) | 25 | 25–12.5 | 50–25 | 25 | 6.2 | 6.2 | 6.2 | 6.2 |
| 3 (d) | >100 | 1.5 | — | 6.2 | 6.2 | 6.2 | 12.5 | 12.5 |
| 3 (l) | 25 | 12.5 | 6.2 | 12.5 | 6.2 | 6.2 | NT | 12.5 |
| 3 (i) | 3.1 | 6.2 | 3.1 | 3.1 | 12.5 | 12.5 | NT | 12.5 |
| Miconazole | 1.5 | 3.1 | 6.2 | 6.2 | 6.2 | 6.2 | 12.5 | 12.5 |

We claim:
1. Compounds of the general formulae:

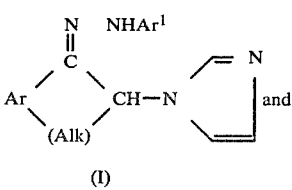

(I)

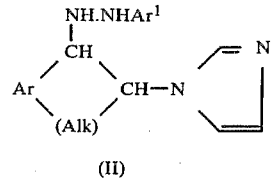

(II)

in which Ar and Ar$^1$ which may be the same or different, represent aromatic radicals optionally substituted once or more than by substituents selected from halogen, lower alkyl and lower alkoxy and Alk represents an alkylene group containing from 1 to 4 carbon atoms which alkylene group may be interrupted with a heteroatom; and acid addition salts thereof.

2. Compounds as claimed in claim 1 in which Ar represents a phenyl group or a thienyl group optionally substituted with one halogen atom.

3. Compounds as claimed in claim 2 in which the halogen atom is a chlorine atom.

4. Compounds as claimed in any of claims 1 to 3 in which Alk is an alkyl group containing 3 or 4 carbon atoms.

5. A compound as claimed in claim 1 which is 2-chloro-6-(1H-imidazol-1-yl)-6,7,8,9-tetrahydro-5-benzocycloheptanone, 2,4-dichlorophenylhydrazone.

6. A compound as claimed in claim 1 which is 6-(1H-imidazol-1-yl)-6,7,8,9-tetrahydro-5-benzocycloheptanone, 2,4-dichlorophenylhydrazone.

7. A compound as claimed in claim 1 which is 2-chloro-6-(1H-imidazol-1-yl)-6,7,8,9-tetrahydro-5-benzocycloheptanone, 2,4,6-trichlorophenylhydrazone.

8. A compound as claimed in claim 1 which is 6-(1H-imidazol-1-yl)-7,8,9,10-tetrahydro-5(6H)-benzocyclooctanone, 2,4-dichlorophenylhydrazone.

9. A compound as claimed in claim 1 which is 7-(1H-imidazol-1-yl)-4,5,6,7-tetrahydro-8H-cyclohepta[b]-thiophen-8-one, 2,4-dichlorophenylhydrazone.

10. A compound as claimed in claim 1 which is 6-(1H-imidazol-1-yl)-7,8,9,10-tetrahydro-5(6H)-benzocyclooctanone, 2,4,6-trichlorophenylhydrazone.

* * * * *